US00PP26819P3

(12) United States Plant Patent
Bédard

(10) Patent No.: US PP26,819 P3
(45) Date of Patent: Jun. 14, 2016

(54) FLORIBUNDA ROSE PLANT NAMED 'WEKNEWCHI'

(50) Latin Name: *Rosa hybrida*
Varietal Denomination: WEKnewchi

(71) Applicant: Early Morning LLC, Pomona, CA (US)

(72) Inventor: Christian Bédard, Placentia, CA (US)

(73) Assignee: EARLY MORNING LLC, Pomona, CA (US)

( * ) Notice: Subject to any disclaimer, the term of this patent is extended or adjusted under 35 U.S.C. 154(b) by 86 days.

(21) Appl. No.: 13/999,067

(22) Filed: Jan. 9, 2014

(65) Prior Publication Data

US 2015/0195967 P1 Jul. 9, 2015

(51) Int. Cl.
*A01H 5/02* (2006.01)

(52) U.S. Cl.
USPC ..... Plt./146

(58) Field of Classification Search
USPC ..... Plt./146, 148, 147, 135, 136
See application file for complete search history.

(56) References Cited

U.S. PATENT DOCUMENTS

PP17,175 P2 10/2006 Carruth
PP18,473 P2 2/2008 Carruth
PP22,587 P2 3/2012 Harkness et al.

OTHER PUBLICATIONS

Tlc Garden Centers Plant Finder Jump for Joy *Rosa* 'Weknewchi' retrieved on Aug. 19, 2015, retrieved from the Internet at <http://plants.tlcgarden.com/12170006/Plant/19479/Jump_For_Joy_Rose> 2 pp.*

Walter Andersen Nursery Garden Talk San Diego's Garden Resource Nov. 2013 retrieved on Aug. 19, 2015, retrieved from the Internet at <http://www.walterandersen.com/wp-content/uploads/2013/11/News1113_F1.pdf> 9 pp.*

Weeks Roses, "2014 Wholesale Catalog", www.weeksroses.com, 2014, 84 pages.

* cited by examiner

*Primary Examiner* — June Hwu
(74) *Attorney, Agent, or Firm* — McKee, Voorhees & Sease PLC

(57) ABSTRACT

A new variety of Floribunda rose suitable for garden decoration, having flowers of peachy pink coloration.

1 Drawing Sheet

Classification: The present invention relates to a new *Rosa hybrida* plant.

Variety denomination: The new plant has the varietal denomination 'WEKnewchi'.

BACKGROUND OF THE INVENTION

This invention relates to a new and distinct variety of Floribunda Rose. It has as its seed parent the variety known as 'WEKlezpat' (U.S. Plant Pat. No. 17,175) and as its pollen parent the variety known as 'WEKvossutono' (U.S. Plant Pat. No. 18,473).

SUMMARY OF THE INVENTION

Among the features which distinguish the new variety from other presently available and commercial rose cultivars known to the inventor are the following combinations of characteristics: its excellent color stability throughout the life of the flower, its moderate fruity and somewhat spicy fragrance and its many hairs on the peduncle and receptacle of the flower. The plant has a rounded bushy growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKnewchi' may be asexually propagated by cuttings, budding and grafting. The budding and grafting successfully occurred on the plant/rootstock *Rosa hybrida* cv. Dr. Huey (not patented).

COMPARISON WITH PARENTS

The new rose may be distinguished from its seed parent, 'WEKlezpat' by the following combination of characteristics: whereas 'WEKnewchi' bears double flowers (about 30 to 40 petals) of peachy pink coloration, 'WEKlezpat' bears very double flowers of butter gold blushed pink coloration with significantly heavier petalage (about 48 to 72 petals). The new variety bears medium sized flowers (about 8.0 to about 10.1 cm. in diameter), whereas the seed parent bears larger flowers (about 7.7 to about 11.8 cm. in diameter).

The new variety may be distinguished from its pollen parent, 'WEKvossutono' by the following combination of characteristics: whereas 'WEKnewchi' bears flowers of peachy pink coloration with a moderate fruity to somewhat spicy fragrance, 'WEKvossutono' bears butter gold flowers with a strong licorice fragrance. The new variety has a rounded bushy medium height growing habit (about 120 to about 200 cm. in height), whereas the pollen parent has a compact and bushy significantly shorter growing habit (about 70 to about 85 cm. in height).

COMPARISON WITH THE CLOSEST COMMERCIALLY AVAILABLE CULTIVAR

The new variety may be distinguished from its closest commercially available cultivar, 'HARpageant' (U.S. Plant Pat. No. 22,587) by the following combination of characteristics: whereas 'WEKnewchi' bears double flowers (about 30 to 40 petals) of peachy pink coloration, 'HARpageant' bears double flowers of mango, peach & apricot blend coloration with significantly lesser petalage (about 20 to 32 petals). The new variety has a rounded bushy growing habit (about 120 to about 200 cm. in height and about 210 to about 250 cm. spread at the widest point), whereas the closest commercially available cultivar has an upright significantly shorter and more compact growing habit (about 100 to about 130 cm. in height and about 50 to about 65 cm. spread at the widest point).

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Pomona, Calif. in the month of December. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of December. Phenotypic expression may vary with environmental, cultural and climatic conditions, as well as differences in conditions of light and soil.

FLOWER

The new variety sometimes bears its flowers singly, sometimes in clusters of two to four per stem. Flowers may be borne in regular rounded clusters on strong moderately short to medium length stems (about 13 to about 60 cm.). The cluster ranges from about 14.5 to about 19.5 cm. in diameter. Outdoors, the plant blooms abundantly and nearly continuously during the growing season. The flowers have a moderate fruity to somewhat spicy fragrance.

BUD

The peduncle is about 3.4 to about 5.0 cm. in length, of average caliper (about 0.3 to about 0.4 cm. in diameter), and usually erect to somewhat stiff. It is smooth with many hairs. Peduncle color is between 146B and 147C often heavily suffused, especially on the side exposed to the sun, with between 187B and 183B.

Before the calyx breaks, the bud is about 1.3 to about 1.7 cm. in diameter at the widest point, about 1.7 to about 2.1 cm. in length, and moderately globular to somewhat ovoid in shape with a conspicuous neck. The surface of the bud bears between 10 to 12 foliaceous appendages with some hairs, usually with slender entire foliaceous parts extending beyond the tip of the bud about ¼ or more of its length. Bud color is between 137C and 138B often moderately suffused, especially on the side exposed to the sun, with between 187B and 183A.

The sepals are about 2.3 to about 3.2 cm. in length and about 0.8 to about 1.1 cm. in width at the widest point. The outer surface color of the sepal is between 137C and 138B often moderately suffused, especially on the side exposed to the sun, with between 187B and 183A. The outer surface of the sepal is smooth and bears between 0 to 6 foliaceous appendages with some hairs. The inner surface color of the sepal is near 146C broadly bordered by near 137A. After the sepals open, the inner surface color is often moderately suffused, especially on the area exposed to the sun, with between 187A and 187B. The inner surface of the sepal is covered with fine wooly tomentum; sepal margins are lined with very few stipitate glands and many hairs.

The receptacle of the flower is of medium length (about 0.7 to about 0.9 cm.) and moderately heavy in caliper (about 0.8 to about 1.1 cm. in diameter). The receptacle is cup-shaped in form. Its surface is smooth with many hairs and with somewhat thin fleshy walls. The receptacle color is between 144A and 138B often moderately suffused, especially on the side exposed to the sun, with between 187B and 183B.

As the petals open (after the calyx breaks), the bud is about 1.6 to about 2.3 cm. in diameter at the widest point, about 2.3 to about 3.2 cm. in length, and moderately ovoid to somewhat pointed in form. The color of the under surfaces of the newly opened petals is between 29B and 24B gradually suffusing toward the petal edge with between 39B and 33B sometimes lightly blushed with between 43C and 46D. At the point where the petal attaches, there is a somewhat large zone of between 154C and 1C. The color of the upper surfaces of the newly opened petals is between 41C and 33B. At the point where the petal attaches, there is a large zone of near 3C.

BLOOM

When fully open, the bloom ranges from about 8.0 to about 10.1 cm. in diameter. Petalage is double with about 30 to 40 petals and about 7 to 15 petaloids irregularly arranged. When partially open, the bloom form is somewhat high centered to cupped, and the petals are loosely spiraled to cupped to somewhat undulated with petal edges somewhat reflexed outward. When fully open, the bloom form is cupped and the petals are loosely cupped to moderately undulated with petal edges somewhat reflexed outward.

PETALS

The substance of the petals is moderately heavy and of medium to somewhat thick thickness, with upper surfaces moderately satiny and under surfaces slightly shiny. The petals are about 3.2 to about 5.2 cm. in length and about 2.6 to about 4.6 cm. in width at the widest point. Petal margins are entire.

The outer petals are moderately obovate to nearly round in shape with rounded to moderately mucronate apices and sometimes slightly notched with one to two notches.

The inner petals are broadly obovate in shape with rounded to moderately mucronate apices.

Petaloids are about 1.3 to about 4.3 cm. in length and about 0.7 to about 3.1 cm. in width at the widest point. Petaloids are irregularly shaped moderately obovate to somewhat oblanceolate with irregular to somewhat rounded apices.

NEWLY OPENED FLOWER

The color at the base of the under surfaces of the outer petals is near 6D gradually suffusing toward the middle of the petal to between 29D and 29C sometimes moderately suffused with between 53B and 53C. There is no visible change in coloration at the point where the petal attaches. The color at the base of the upper surfaces of the outer petals is between 10B and 8B gradually suffusing toward the middle of the petal to between 33D and 29C sometimes moderately suffused with between 53B and 53C. There is no visible change in coloration at the point where the petal attaches.

The color at the base of the under surfaces of the intermediate and inner petals is near 6D gradually suffusing toward the middle of the petal to between 29D and 29C sometimes lightly suffused with between 53C and 53D. The color at the base of the upper surfaces of the intermediate and inner petals is between 10B and 8B gradually suffusing toward the middle of the petal to between 33D and 29C sometimes lightly suffused with between 53C and 53D.

The under and upper surface colors of the petaloids are similar in coloration to the upper and under surfaces of the intermediate and inner petals.

The general tonality of the newly opened flower is between 10B and 8B at the base gradually suffusing toward the middle of the petal to between 33D and 29C.

THREE-DAY-OLD FLOWER

The color at the base of the under surfaces of the outer petals is near 10D gradually suffusing toward the middle of the petal to between 27A and 36A sometimes moderately suffused with between 60C and 60D. There is no visible change in coloration at the point where the petal attaches. The color at the base of the upper surfaces of the outer petals is between 8C and 4C gradually suffusing toward the middle of the petal to between 37D and 36A sometimes moderately suffused with between 60A and 60B. There is no visible change in coloration at the point where the petal attaches.

The color at the base of the under surfaces of the intermediate and inner petals is near 10D gradually suffusing toward the middle of the petal to between 27A and 36A sometimes lightly suffused with between 60C and 60D. The color at the base of the upper surfaces of the intermediate and inner petals is between 8C and 4C gradually suffusing toward the middle of the petal to between 37D and 36A sometimes moderately suffused with between 60A and 60B.

The under and upper surface colors of the petaloids are similar in coloration to the upper and under surfaces of the intermediate and inner petals.

The general tonality of the three-day-old flower is between 8C and 4C at the base gradually suffusing toward the middle of the petal to between 37D and 36A.

On the spent bloom, the petals usually drop off cleanly.

In December in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 150) and are arranged regularly about the pistils; a few are mixed with petaloids. The filaments are of medium to somewhat long length (about 0.4 to about 1.1 cm.) most with anthers. Filaments are between 14B and 13A in color. The anthers are moderately small for the class and all open approximately at the same time. Anther color when immature is near 23B on the external part and near 12D on the internal part. Anther color at maturity is near 164C on the external part and near 200A on the internal part. Pollen is moderate and between 18C and 19C in color.

FEMALE REPRODUCTIVE ORGANS

Pistils vary in number (average about 130). The styles are moderately even, somewhat short to average in length (about 0.4 to about 0.7 cm.), thin in caliper and loosely bunched to somewhat separated. Stigma color is between 14C and 11A. Style color is between 2D and 1D often lightly suffused with between 53B and 53C. Ovaries are usually all enclosed in the calyx.

Hips are of average length (about 1.2 to about 1.7 cm.), rounded to somewhat globular in form with a flat top, and between 26A and 25A in color when ripe. The hip surface is smooth with thick fleshy walls. The sepals are moderately permanent and usually straight in shape.

The seeds are irregularly rounded, smooth in texture, approximately 11 to about 17 per hip, about 0.5 to about 0.7 cm. in diameter at the widest point and between 164C and 165D in color.

FOLIAGE

The compound leaves are usually comprised of three to seven leaflets and are borne abundantly. The five-leaflet leaves are about 7.0 to about 11.8 cm. in length and about 4.8 to about 9.1 cm. in width at the widest point, moderately leathery to somewhat crisp in texture, and glossy in finish on the upper side and semi-glossy to somewhat matte in finish on the underside. The leaves have a pinnate venation pattern. The terminal leaflets are about 3.1 to about 5.5 cm. in length and about 2.1 to about 3.5 cm. in width at the widest point, shaped ovate to somewhat oval with acute to somewhat acuminate apices and rounded bases. Their margins are usually simply serrate.

The upper surface color of the mature leaf is between 139A and 147A. The under surface color of the mature leaf is between 147B and 148C. The under and upper colors of the leaf veins on the mature leaf are similar in coloration to the upper and under surfaces colors of the mature leaf. The upper surface color of the young leaf is between 137A and 147A, often heavily suffused with between 187A and 183A. The under surface color of the young leaf is between 138B and 139C, often moderately suffused with between 187B and 183A. The under and upper colors of the leaf veins on the young leaf are similar in coloration to the upper and under surfaces colors of the young leaf.

The rachis is somewhat light in caliper and rough. The upper side is shallowly grooved with few hairs and stipitate glands on the edges of the grooves. The under side of the rachis is rough with few stipitate glands and small prickles. The rachis color is near 146D on the underside and near 137C on the upper side often moderately suffused on the young leaves with between 187B and 183B.

The stipules are about 1.0 to about 1.8 cm. in length and moderately wide (about 0.5 to about 0.9 cm.) with moderately long straight points that usually turn out at an angle of more than 45 degrees and sometimes recurve toward the stem. The under and upper surface color of the stipule is between 137C and 146B often moderately suffused on the young leaves with between 187B and 183B.

The petiole is somewhat light in caliper and rough. The upper side is shallowly grooved with few hairs and stipitate glands on the edges of the grooves. The under side of the petiole is rough with few stipitate glands and small prickles. The petiole is about 0.5 to about 1.6 cm. in length and about 0.1 to about 0.2 cm in width at the widest point. The petiole color is near 146D on the underside and near 137C on the upper side often moderately suffused on the young leaves with between 187B and 183B.

The plant displays an above average degree of resistance to powdery mildew and rust as compared to other commercial varieties grown under comparable conditions in Pomona, Calif. The plant's winter hardiness and drought/heat tolerance are yet to be determined.

GROWTH

The plant has a rounded bushy medium height growing habit (about 120 to about 200 cm. in height and about 210 to about 250 cm. spread at the widest point), with very full branching. It displays moderately vigorous growth and the canes are of somewhat heavy caliper for the class (about 2.3 to about 3.5 cm. in diameter at the widest point).

The color of the major stems is between 147B and 146A. They bear some large prickles that are about 0.5 to about 0.7 cm. in length. The large prickles are hooked slightly downward with a somewhat short moderately broad oval base; prickle color is between 164A and 165B. The major stem bears few small prickles of similar shape and coloration.

The color of the branches is between 146B and 147B. They bear few large prickles which are of similar size and shape to the large prickles on the major stems; prickle color is between 162C and 161C often moderately suffused with between 187C and 187D. The branches bear few small prickles of similar shape and coloration.

The color of the new shoots is between 146C and 147C often heavily suffused with between 187B and 183A. They bear few large prickles which are of similar size and shape to the large prickles on the major stems; prickle color is between 162C and 161C often heavily suffused with between 187B and 187C to as dark as near 187A. The shoots bear few small prickles of similar shape and coloration.

I claim:

1. A new and distinct Floribunda rose plant of the variety substantially as described and illustrated herein.

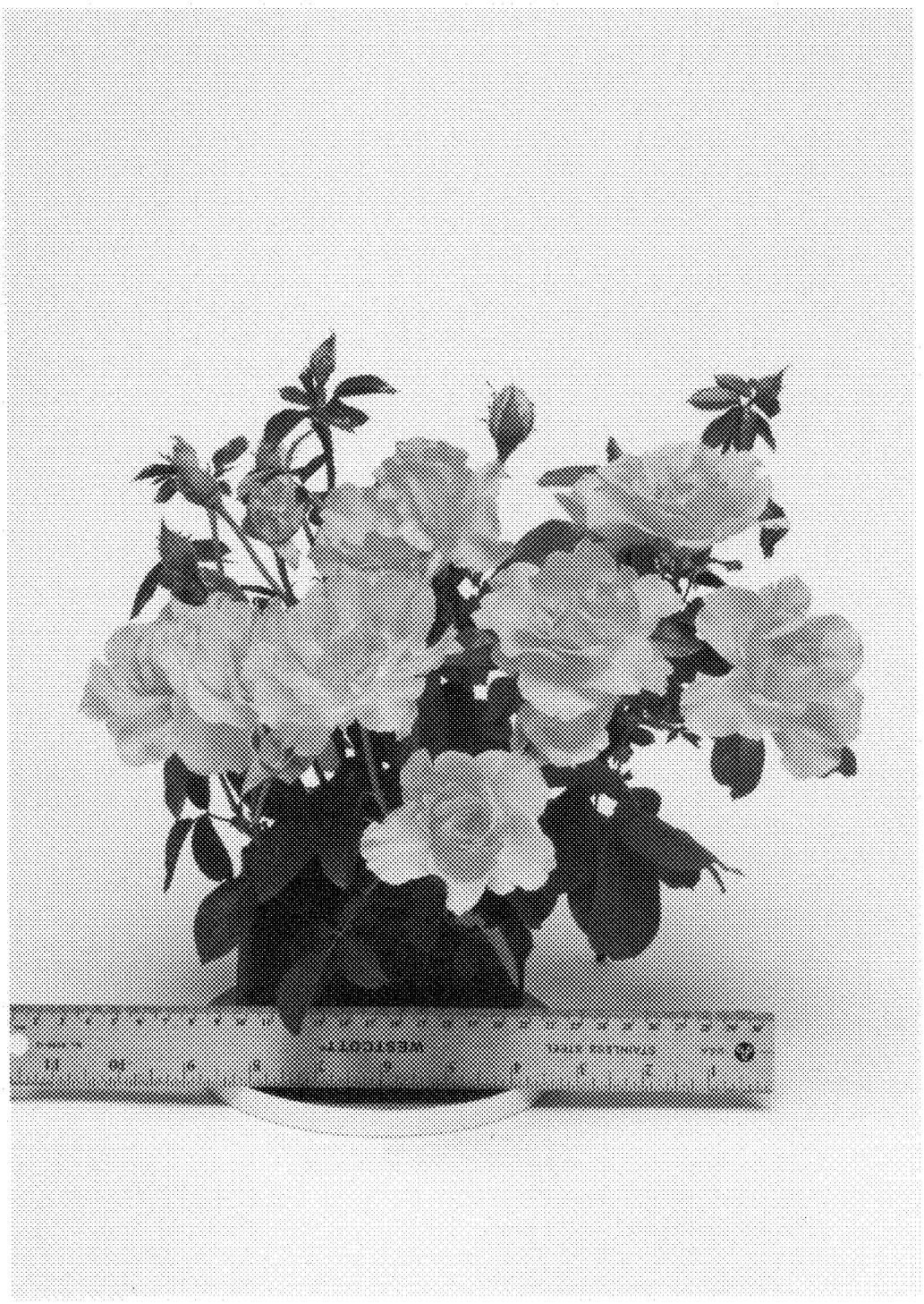

* * * * *